US008251914B2

(12) United States Patent
Daniels et al.

(10) Patent No.: US 8,251,914 B2
(45) Date of Patent: *Aug. 28, 2012

(54) RESPIRATORY PROFILE PARAMETER DETERMINATION METHOD AND APPARATUS

(75) Inventors: Rich H. Daniels, Wallingford, CT (US); John R. Delfavero, East Hampton, CT (US); Barry J. Feldman, Cheshire, CT (US); Paul B. Gunneson, Wallingford, CT (US); Michael B. Jaffe, Cheshire, CT (US); Eric P. Wigforss, Durham, CT (US)

(73) Assignee: RIC Investments, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/645,994

(22) Filed: Dec. 23, 2009

(65) Prior Publication Data

US 2010/0097380 A1 Apr. 22, 2010

Related U.S. Application Data

(60) Continuation of application No. 10/271,856, filed on Oct. 15, 2002, now Pat. No. 7,662,106, which is a continuation of application No. 09/733,776, filed on Dec. 8, 2000, now Pat. No. 6,471,658, which is a continuation of application No. 09/334,778, filed on Jun. 16, 1999, now Pat. No. 6,179,784, which is a division of application No. 08/963,394, filed on Nov. 3, 1997, now Pat. No. 6,099,481.

(51) Int. Cl.
*A61B 5/08* (2006.01)

(52) U.S. Cl. .......................... 600/532; 600/538; 600/529
(58) Field of Classification Search .......... 600/529–543, 600/484; 128/204.23; 73/23.3
See application file for complete search history.

(56) References Cited

U.S. PATENT DOCUMENTS

| 3,896,792 | A | | 7/1975 | Vail et al. ..................... 600/532 |
| 4,047,521 | A | | 9/1977 | Kramer et al. |
| 4,269,194 | A | * | 5/1981 | Rayburn et al. ............... 600/532 |
| 4,403,514 | A | | 9/1983 | Osborn |
| 4,440,177 | A | | 4/1984 | Anderson et al. ............. 600/532 |
| 4,463,764 | A | | 8/1984 | Anderson et al. |
| 4,671,297 | A | | 6/1987 | Schulze, Jr. |
| 4,685,464 | A | | 8/1987 | Goldberger et al. |
| 4,825,879 | A | | 5/1989 | Tan et al. |
| 4,830,014 | A | | 5/1989 | Goodman et al. |
| 4,859,858 | A | | 8/1989 | Knodle et al. |
| 4,859,859 | A | | 8/1989 | Knodle et al. |
| 4,865,038 | A | | 9/1989 | Rich et al. |
| 4,914,720 | A | | 4/1990 | Knodle et al. |

(Continued)

OTHER PUBLICATIONS

Sullivan, et al., *Pneumotachographs: Theory and Clinical Application*, Respiratory Care, vol. 29-7, pp. 736-749 (1984).

*Primary Examiner* — Navin Natnithithadha

(57) ABSTRACT

A method of sampling one or more respiratory profile characteristics and monitoring a variety of respiratory profile parameters. The sampled respiratory characteristics include respiratory flow rate, respiratory pressure, and partial pressure of at least one constituent of a patient's respiration. The method detects patient breaths, determines whether each breath is a spontaneous breath or a ventilator-induced breath and calculates various respiratory profile parameters based on the sampled measurements. The method displays the respiratory profile parameters in graphic and numeric forms. Preferably, the method allows a user to select the displayed respiratory profile parameters.

22 Claims, 12 Drawing Sheets

U.S. PATENT DOCUMENTS

| | | | |
|---|---|---|---|
| 4,941,476 A | 7/1990 | Fisher | 600/532 |
| 4,947,860 A | 8/1990 | Fisher | 600/532 |
| 4,958,075 A | 9/1990 | Mace et al. | |
| 4,989,456 A | 2/1991 | Stupecky | |
| 5,038,773 A | 8/1991 | Norlien et al. | |
| 5,052,395 A | 10/1991 | Burton et al. | |
| 5,088,332 A | 2/1992 | Merilainen et al. | |
| 5,129,401 A | 7/1992 | Corenman et al. | 600/529 |
| 5,146,092 A | 9/1992 | Apperson et al. | |
| 5,153,436 A | 10/1992 | Apperson et al. | |
| 5,170,786 A | 12/1992 | Thomas et al. | |
| 5,197,481 A | 3/1993 | Fisher | 600/532 |
| 5,206,511 A | 4/1993 | Apperson et al. | |
| 5,206,807 A | 4/1993 | Hatke et al. | 600/484 |
| 5,209,230 A | 5/1993 | Swedlow et al. | |
| 5,217,012 A | 6/1993 | Young et al. | |
| 5,251,121 A | 10/1993 | Knodle et al. | |
| 5,273,036 A | 12/1993 | Kronberg et al. | |
| 5,299,579 A * | 4/1994 | Gedeon et al. | 600/532 |
| 5,316,009 A | 5/1994 | Yamada | 600/533 |
| 5,320,093 A | 6/1994 | Raemer | 128/203.12 |
| 5,337,744 A | 8/1994 | Branigan | |
| 5,347,843 A | 9/1994 | Orr et al. | |
| 5,355,893 A * | 10/1994 | Mick et al. | 600/532 |
| 5,379,650 A | 1/1995 | Kofoed et al. | |
| 5,402,796 A * | 4/1995 | Packer et al. | 600/532 |
| 5,405,269 A | 4/1995 | Stupecky | |
| 5,438,986 A | 8/1995 | Disch et al. | |
| 5,469,845 A | 11/1995 | DeLonzor et al. | |
| 5,533,512 A | 7/1996 | Novotny et al. | 600/532 |
| 5,535,633 A | 7/1996 | Kofoed et al. | |
| 5,632,281 A | 5/1997 | Rayburn | 600/532 |
| 5,765,563 A | 6/1998 | Vander Schaaf | 600/538 |
| 5,772,599 A | 6/1998 | Nevo et al. | 600/483 |
| 5,800,361 A | 9/1998 | Rayburn | 600/532 |
| 5,836,300 A | 11/1998 | Mault | 128/204.23 |
| 5,881,723 A | 3/1999 | Wallace et al. | 128/204.21 |
| 5,915,379 A | 6/1999 | Wallace et al. | 128/204.21 |
| 5,915,380 A | 6/1999 | Wallace et al. | 128/204.21 |
| 6,024,089 A | 2/2000 | Wallace et al. | 128/204.21 |
| 6,099,481 A | 8/2000 | Daniels et al. | 600/538 |
| 6,135,107 A | 10/2000 | Mault | 128/204.23 |
| 6,142,149 A | 11/2000 | Steen | 128/204.23 |
| 6,174,289 B1 | 1/2001 | Binder | 600/532 |
| 6,179,784 B1 | 1/2001 | Daniels et al. | 600/538 |
| 6,234,963 B1 | 5/2001 | Blike et al. | |
| 6,251,082 B1 | 6/2001 | Rayburn | 600/532 |
| 6,302,851 B1 * | 10/2001 | Gedeon | 600/538 |
| 6,305,373 B1 | 10/2001 | Wallace et al. | 128/204.21 |
| 6,306,098 B1 | 10/2001 | Orr et al. | 128/200.26 |
| 6,360,745 B1 | 3/2002 | Wallace et al. | 128/204.21 |
| 6,369,838 B1 | 4/2002 | Wallace et al. | 715/810 |
| 6,468,222 B1 | 10/2002 | Mault et al. | 600/531 |
| 6,471,658 B1 | 10/2002 | Daniels et al. | 600/538 |
| 6,648,832 B2 | 11/2003 | Orr et al. | 600/532 |

* cited by examiner

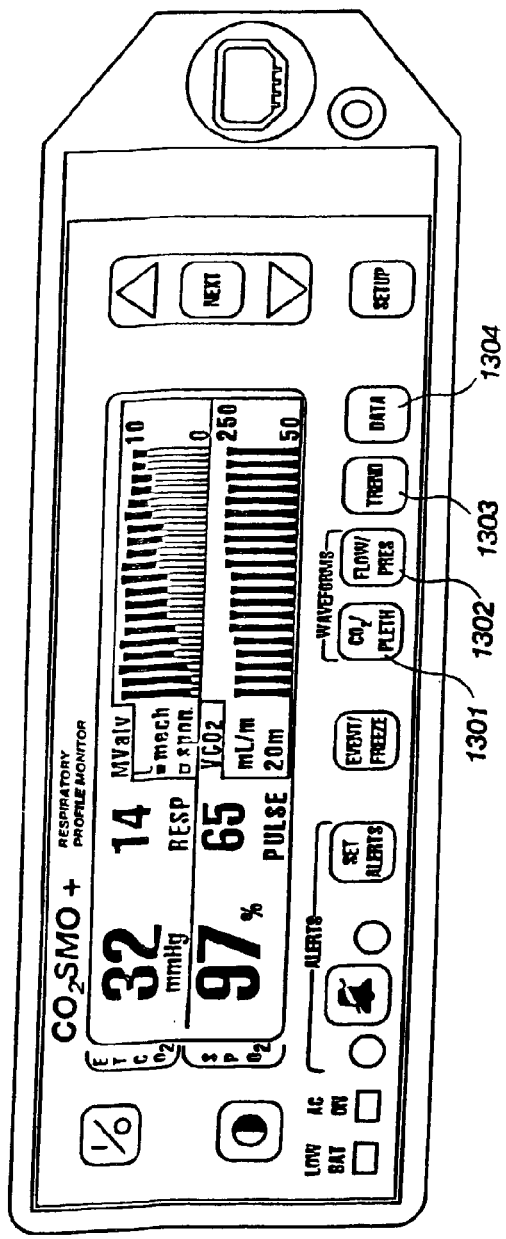
*Fig. 13*
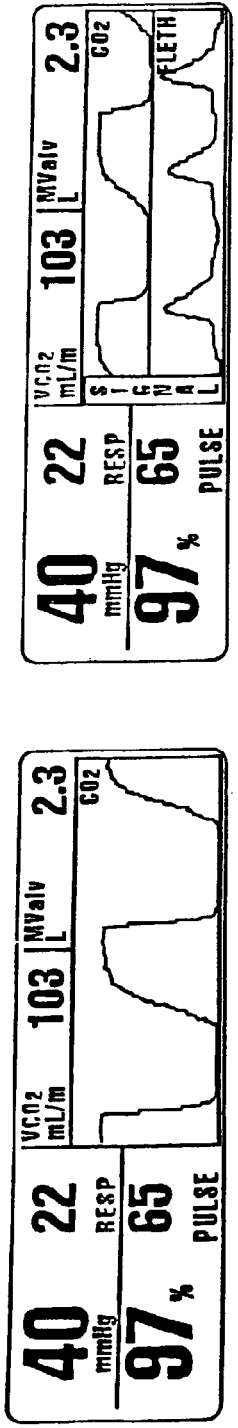
*Fig. 15*
*Fig. 14*

RESPIRATORY PROFILE PARAMETER DETERMINATION METHOD AND APPARATUS

CROSS-REFERENCE TO RELATED APPLICATIONS

This application is a continuation of application Ser. No. 09/733,776, filed Dec. 8, 2000, pending, which is a continuation of application Ser. No. 09/334,778, filed Jun. 16, 1999, now U.S. Pat. No. 6,179,784, issued Jan. 30, 2001, which is a divisional of application Ser. No. 08/963,394, filed Nov. 3, 1997, now U.S. Pat. No. 6,099,481, issued Aug. 8, 2000.

BACKGROUND OF THE INVENTION

1. Field of the Invention

The present invention relates to systems which monitor both airway carbon dioxide concentration and respiratory flow. Specifically, the present invention relates to systems which monitor respiratory air flow, pressure and carbon dioxide levels, process those measurements to derive information about various respiratory-related functions and blood carbon dioxide levels, and display the measured and derived information.

2. State of the Art

Respiratory monitors are known in the art. Typically, respiratory monitors measure respiratory air flow rates at discrete sampling intervals. Many respiratory monitoring apparatus process respiratory samples to determine characteristics such as respiratory rate and depth of respiration. U.S. Pat. Nos. 5,273,036, issued to Harald Kronberg and Helmut Leist on Dec. 28, 1993 and U.S. Pat. No. 4,989,456, issued to Josef Stupecky on Feb. 5, 1991, disclose exemplary devices.

However, many respiratory monitors in the prior art sample only a limited aspect of a patient's respiration and display a limited number of directly measured respiratory characteristics rather than an overall profile of a patient's respiration. Moreover, many existing respiratory monitors do not allow a user to select the displayed respiratory profiles.

A system is needed which monitors a variety of respiratory profile parameters and displays data regarding those parameters. There is also a need for a system which, following measurement of some respiratory parameters, automatically generates data regarding other respiratory profile parameters.

BRIEF SUMMARY OF THE INVENTION

The system of the present invention addresses the foregoing needs. The system of the present invention includes an apparatus which utilizes software to process respiratory pressure, flow, volume and gas content information and preferably displays such types of information in the forms of numeric values and graphs. The system of the present invention also processes the measured information in order to calculate or otherwise determine a wide variety of respiratory profile characteristics which are not directly measurable by noninvasive means.

In a preferred embodiment of the method of the present invention, respiratory measurements are taken at discrete time intervals. Preferably, respiratory samples are taken about once every 0.01 seconds (10 milliseconds). The respiratory measurements taken during each sample include, but are not limited to, the respiratory flow rate, respiratory pressures, respiratory carbon dioxide level, and other respiratory or respiratory-related characteristics. Blood oxygen saturation may also be measured by the system of this invention. Pulse oximetry methods which are known to those in the art are preferred for measuring blood oxygen saturation in connection with the present invention. Each piece of data is either sampled digitally or sampled by analog means, then digitized immediately following sampling. Methods and mechanisms for digital sampling and digitization of analog samples which are known to those of ordinary skill in the art are useful in the system of the present invention.

During respiratory monitoring and sampling, the system of the present invention calculates various respiratory profile characteristics, including, without limitation, the timing of the respiratory cycle and its intervals, respiratory flows and volumes, respiratory pressures, and carbon dioxide levels in the breath. The derivation of carbon dioxide and oxygen levels in a patient's arterial blood are also within the contemplated scope of the present invention. If a patient's respiration is controlled by a ventilator, the system of the present invention may also calculate respiratory mechanics characteristics.

Other advantages of the respiratory profile parameter processing and display system of the present invention will become apparent to those of skill in the relevant art through a consideration of the ensuing description and the appended drawing figures.

BRIEF DESCRIPTION OF THE SEVERAL VIEWS OF THE DRAWINGS

FIG. 13 depicts a respiratory profile monitor that is useful for taking respiratory measurements in accordance with the present invention;

FIG. 14 depicts a capnogram;

FIG. 15 depicts a plethysmogram;

DETAILED DESCRIPTION OF THE INVENTION

The present invention includes a system for detecting and processing data of various respiratory flow and blood gas parameters. Apparatus which monitor respiratory flow and blood gas data are used to detect air flow pressures, air flow volumes, partial carbon dioxide pressure, and other breath characteristics. The method of the present invention is then employed to analyze the collected data, process the data to derive values for other respiratory characteristics, and display the collected and derived data.

Data Collection

Figure 1:
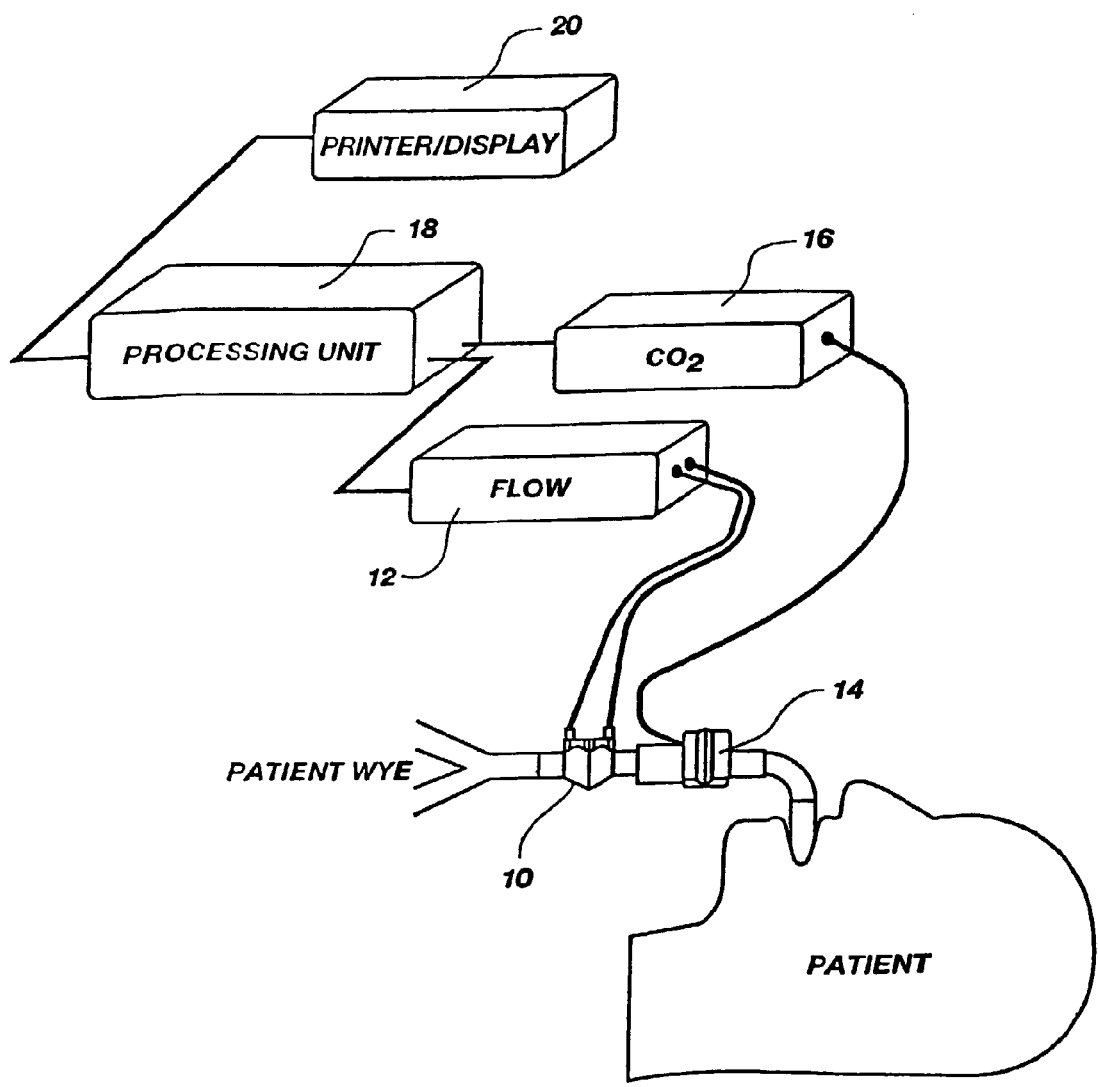
FIG. 1 is a schematic illustration of a system which measures respiratory flow, pressure and gas content samples.

Preferably, the inventive system, illustrated schematically in FIG. 1, includes a differential pressure flowmeter, which is also referred to as a pneumotachometer 10, a flow signal unit 12, a gas ($CO_2$) sensor 14, a $CO_2$ signal unit 16, a processing unit 18 and a data printer/display 20. This system can be used whether or not the patient is mechanically ventilated.

Many devices for measuring the volume of a person's expiratory breath already possess the capability to integrate a measured flow and can be used with the present invention. Typically, flow measuring devices use one of the following methods to determine flow:

1. measurement of pressure drop or differential pressure across a fixed resistance (differential pressure flowmeter or pneumotachometer),
2. measurement of the temperature change of a heated wire cooled by the airflow (hot wire anemometer),
3. measurement of frequency shift of an ultrasonic beam passed through the airstream (ultrasonic Doppler),
4. counting the number of vortices shed as air flows past a strut (vortex shedding), or
5. measurement of transmission time of a sound or heat impulse created upstream to a downstream sensor (time of flight device).

Alternatively, volume may be measured directly by counting revolutions of a vane placed in the respiratory flow path (e.g., a spinning vane). A discussion of the aforementioned devices and associated technology can be found in Sullivan, et al., *Pneumotachographs: Theory and Clinical Application*, Respiratory Care, Vol. 29-7, pages 736-749 (1984), which is incorporated herein by reference. Examples of known differential pressure flowmeters include those described in U.S. Pat. Nos. 4,047,521, 4,403,514, 5,038,773, 5,088,332, 5,347, 843, 5,379,650 and 5,535,633, the disclosures of each of which are incorporated herein by reference.

The exemplary device for respiratory flow measurement is the differential pressure flowmeter 10 or "pneumotachometer", which provides a pressure differential indicative of respiratory flow, the differential pressure being converted via pressure transducers in flow signal unit 12 to electrical signals which are subsequently processed to provide flow rate and volume by processing unit 18. The flowmeter 10 is preferably the Pediatric/Adult Combined $CO_2$/Flow Sensor (Catalog No. 6719) or the Neonatal Combined $CO_2$/Flow Sensor (Catalog No. 6720), manufactured and sold by Novametrix Medical Systems, Inc., Wallingford, Conn. However, any of the aforementioned types of flow measurement devices may be utilized in the inventive system.

Sensors that are capable of measuring the partial pressure of carbon dioxide content in a patient's breath are well known. The currently preferred device for measuring breath carbon dioxide content is a gas analyzer of the type employing non-dispersive infrared radiation which presents data representing the % $CO_2$ (or $pCO_2$) of a sample of exhaled breath. Examples of known infrared gas analyzers include those described in U.S. Pat. Nos. 4,859,858, 4,859,859, 4,914,720, 4,958,075, 5,146,092, 5,153,436, 5,206,511 and 5,251,121, the disclosures of each of which are incorporated herein by reference. Other technologies used to measure the concentration of carbon dioxide, such as Raman spectroscopy and mass spectroscopy, can also be used in connection with the system of the present invention.

An exemplary gas sensor 14 that is capable of measuring carbon dioxide content in a patient's exhaled breath is available from Novametrix Medical Systems, Inc., Wallingford, Conn., under the trade name CAPNOSTAT™. Other methods of measuring carbon dioxide content, both at the airway (mainstream) or by removing a sample (sidestream), are known to those of ordinary skill in the art and are useful with the system of the present invention.

Gas analyzers of the types described above employ non-dispersive infrared radiation to measure the concentration of a selected gas in a mixture of gases. The infrared radiation can be emitted from a thick film source and focused by a mirror to pass through the mixture of gases being analyzed. After passing through the gas mixture, the infrared beam passes through a filter which reflects all of the radiation wavelengths except for those in the narrow bands centered around the wavelength which is absorbed by the gas of concern (such as $CO_2$) in the mixture being analyzed (such as the air flow from a person's expired breath). This narrow band of radiation, which typically extends approximately 190 angstroms to each side of the wavelength on which the radiation is centered, reaches a detector which is capable of producing an electrical output signal proportional to the magnitude of the infrared radiation impinging upon it, as the radiation in that band is attenuated to an extent which is proportional to the concentration of the designated gas in the mixture of gases being analyzed. The strength of the signal generated by the detector is inversely proportional to the concentration of the designated gas and can be inverted to provide a signal indicative of that concentration.

Non-invasive pulse oximetry sensors ($SpO_2$) that are capable of measuring a patient's pulse and the oxygen content of a patient's arterial blood are well known and may be used in the system of the present invention. Examples of known $SpO_2$ sensors include those described in U.S. Pat. Nos. 4,685, 464, 4,825,879, 4,830,014, 4,865,038, 4,928,691, 5,170,786, 5,209,230, 5,217,012, 5,337,744, 5,469,845, and 5,438,986, the disclosures of each of which are incorporated herein by reference. Preferably, a non-invasive $SpO_2$ sensor, such as that sold under the trade name SUPERBRIGHT® by Novametrix Medical Systems, Inc., is used in the system of this invention. Other technologies used to measure pulse and/or arterial blood $O_2$ saturation can also be used in connection with the system of the present invention.

Processing unit 18 may be either a programmed personal computer employing a microprocessor in combination with a suitable digital interface for receiving the digital signals from the $CO_2$ signal unit 16 and flow signal unit 12, or any specially designed processor unit programmed as to be capable of calculating the respiratory parameters as disclosed further herein. Processing unit 18 may also direct the storage of all of the calculated respiratory parameters. An exemplary processor/display unit which has been designed specifically for such purposes is the processor sold under the trade name $CO_2SMO$® Plus! by Novametrix. Display 20 is any display that will display graphic information and/or numeric data as directed by processing unit 18. For example, when processing unit 18 is a personal computer, any compatible video monitor may be used as display 20. Display 20 may also include a mechanism which audibly alerts a user about various patient respiratory information. When processing unit 18 is a personal computer, any sound card and speaker which is compatible therewith will impart the system of the present invention with the ability to generate audible warnings and alarms.

Processing unit 18 is programmed to perform the method of the present invention, as set forth hereinbelow. Thus, processing unit 18 includes a plurality of logic circuits for performing the process of the present invention.

Data Processing and Storage

Figures 2, 3:
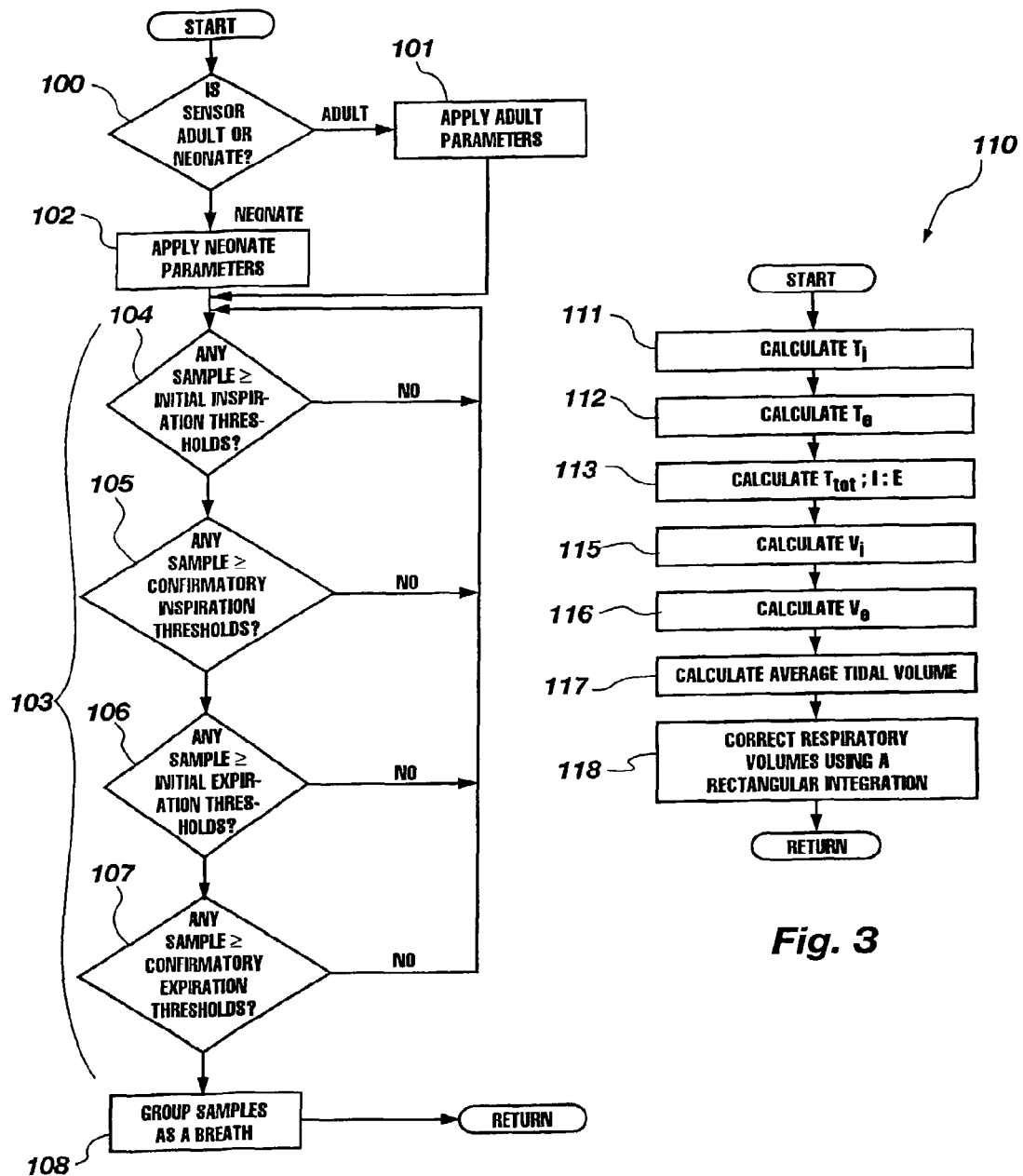
FIG. 2 is a flow chart of a preferred process for identifying and storing sampled data of a patient breath.
FIG. 3 is a flow chart of a method of calculating respiratory time and volume parameters.

Referring now to the flow chart of FIG. 2, processing unit 18, in performance of the method, inquires at 100 whether the air flow sensor is an adult sensor or a neonatal sensor. If the sensor is a neonatal respiratory sensor, a neonatal sensor parameter set is applied to the monitored data as shown at 102. Otherwise, an adult sensor parameter set is applied to the data, as shown at 101.

Next, as shown at 103, a determination is made of whether a series of respiratory samples taken since the patient's last breath comprise a patient breath. Depending upon whether the patient is a neonate or an adult, certain threshold pressures and volumes are required during both inhalation and exhalation in order for a set of samples to be considered as a breath. First, as described in further detail below with reference to FIG. 3, using techniques which are known in the art, flow rate and fluid volumes are calculated from pressure and timing measurements. A determination is then made of whether any of the samples equaled or exceeded an initial inhalation threshold pressure level and an initial inhalation threshold volume level, as shown at 104. Then a determination is made, as shown at inquiry 105, whether the inspiration pressure and volume for a subsequent respiratory sample equaled or exceeded the inspiration confirmation thresholds. Next, the respiratory flow for subsequent respiratory samples must meet both initial and confirmatory expiration pressure and volume thresholds, as shown at inquiries 106 and 107, respectively. If neither of the thresholds were met in any of the four preceding inquiries, no breath is detected, and the sampled data is not recognized by the system as a breath. The system of the present invention continues to monitor respiratory flow and pressure until a breath is detected. When each of the four sets of thresholds have been met, a breath has been detected and the respiratory samples are identified as part of a breath, as shown at 108. The respiratory flow, pressure, gas levels and timing of the sample are then stored and processed.

The sampled pressure and gas ($CO_2$) levels for each breath and the time interval between samples are processed to determine various other respiratory parameters, including, but not limited to, duration of the breathing cycle, respiratory flow and volume characteristics, respiratory pressure characteristics, respiratory mechanics, carbon dioxide levels and related respiratory parameters.

FIG. 3 illustrates a preferred process for the collection of timing data, referred to collectively as step 110. The invention measures respiratory volume and pressure at specific time intervals.

Figure 4:
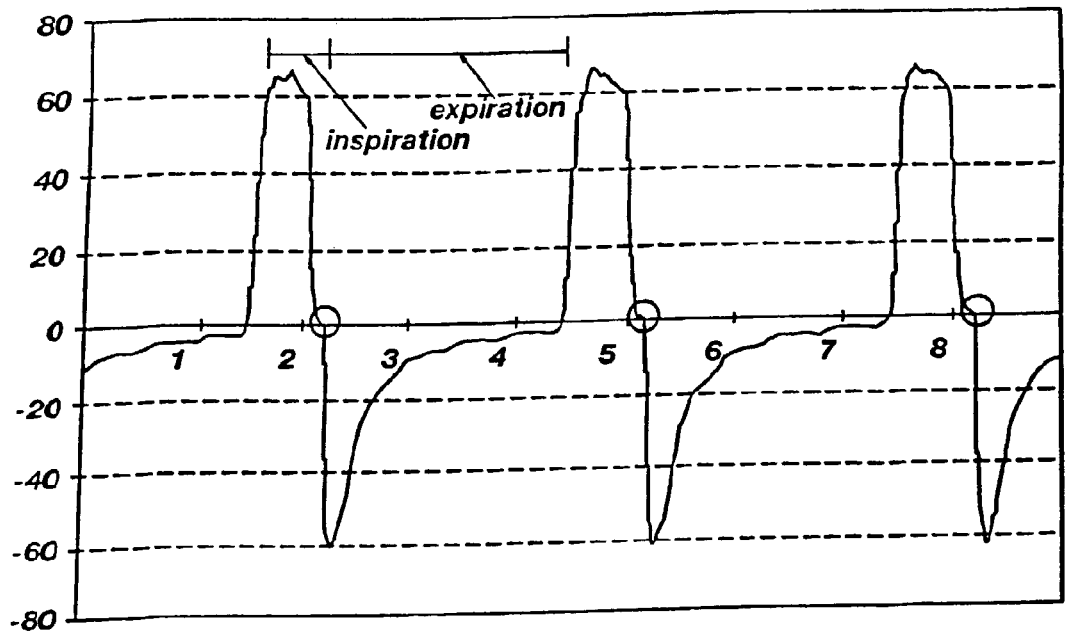
FIG. 4 depicts a respiratory flow waveform.

FIG. 4 is a graph, referred to as a respiratory flow waveform, which illustrates respiratory flow rates over time. Airflow into a patient's lungs is measured as positive airflow. Airflow out of a patient's lungs is measured as negative airflow. The beginning of inspiration is measured as respiratory airflow increases from about zero liters per minute (LPM). Inspiration continues until an inspiratory pause, when the airflow decreases, returning to about zero LPM. At about the point where airflow becomes negative, exhalation begins. Exhalation continues until the air flow reaches about zero LPM.

Referring again to FIG. 3, the inspiratory time ($T_i$) is measured as shown at 111. $T_i$ is the length of time of the inspiratory phase of ventilation, typically when respiratory air flow is greater than about zero. Thus, $T_i$ is equal to the difference in time between the first and last respiratory samples of each inspiratory period. As shown at 112, the expiratory time ($T_e$) is measured. $T_e$ is the time duration of the expiratory phase of ventilation, typically when respiratory air flow is less than about zero. Thus, $T_e$ is equal to the difference in time between the first and last samples of each expiratory period. The entire ventilatory period, also referred to as the total cycle time ($T_{tot}$), is calculated as shown at 113, by adding $T_i$ and $T_e$. $T_{tot}$ is the time from the start of inspiration of one detected breath to the start of inspiration for the subsequent detected breath. The ratio of inspiratory time to expiratory time (I:E) is also calculated as shown at 113 using the summed $T_i$ and $T_e$ for all detected breaths. Preferably, I:E is updated with each new detected breath.

The inspiratory volume ($V_i$), which is the volume of gas inhaled during the inspiratory phase of a detected breath, is determined as shown at 115. One method of calculating inspiratory volume includes summing the products of flow rate multiplied by the time interval between samples of each respiratory sample during an inspiratory phase. That measurement is stored. Other methods for determining $V_i$ are also within the scope of the method of the present invention.

The volume of expired gas, also referred to as the expiratory volume ($V_e$), is determined as shown at 116. One method of calculating expiratory volume includes summing the products of flow rate multiplied by the time interval between samples of each respiratory sample during the expiratory phase, with trapezoidal integration of the samples. That measurement is then stored. Another method for calculating expiratory volume includes averaging the flow rates of each sample during the expiratory phase, then multiplying that value by $T_e$. Other methods for determining $V_e$ are also within the scope of the method of the present invention. As shown at 117, the average tidal volume is calculated by averaging the $V_e$ values over the lesser of the last eight breaths, or all of the complete breaths within the last minute.

Various factors, including, without limitation, zero point drift, coughing, swallowing, cardiogenic oscillations, and others, inhibit the automatic determination of the four breathing cycle phases. Thus, a preferred embodiment of the method of the present invention utilizes a dual level flow detection algorithm to minimize sensitivity to such factors. As shown at 118, respiratory volumes are computed using rectangular integration or trapezoidal integration (i.e., the running sums of the sampled volumes are scaled by the sampling interval).

Figure 5:
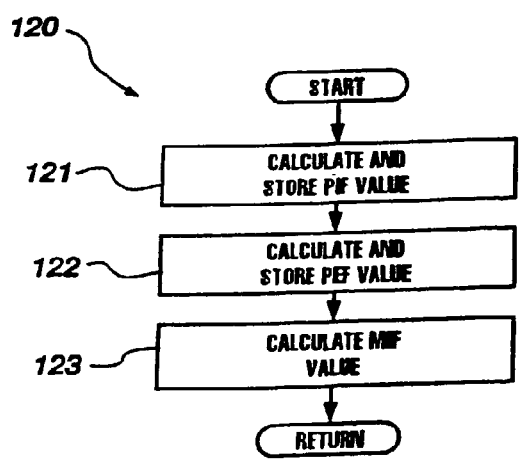
FIG. 5 is a flow chart of a method of calculating respiratory flow parameters.

With reference to FIG. 5, the determination of various flow and volume data measurements are made, referred to collectively as step 120. The largest inspiratory flow sample (i.e., highest positive flow value) measured for each detected breath is referred to as the peak inspiratory flow (PIF) value for that breath. The PIF value for the last detected breath is determined and stored as shown at 121. Similarly, the largest expiratory flow sample (i.e., lowest negative flow value) measured for each detected breath is referred to as the peak expiratory flow (PEF) value for that breath. The PEF value of the last detected breath is determined and stored as shown at 122. Mean inspiratory flow (MIF) is calculated as shown at 123. MIF is determined by averaging each of the sampled flow values during the entire inspiratory phase. Preferably, MIF is calculated using inspiratory flow samples from each of the lesser of the last eight detected breaths, or from each of the detected breaths over the last minute.

Figure 6:
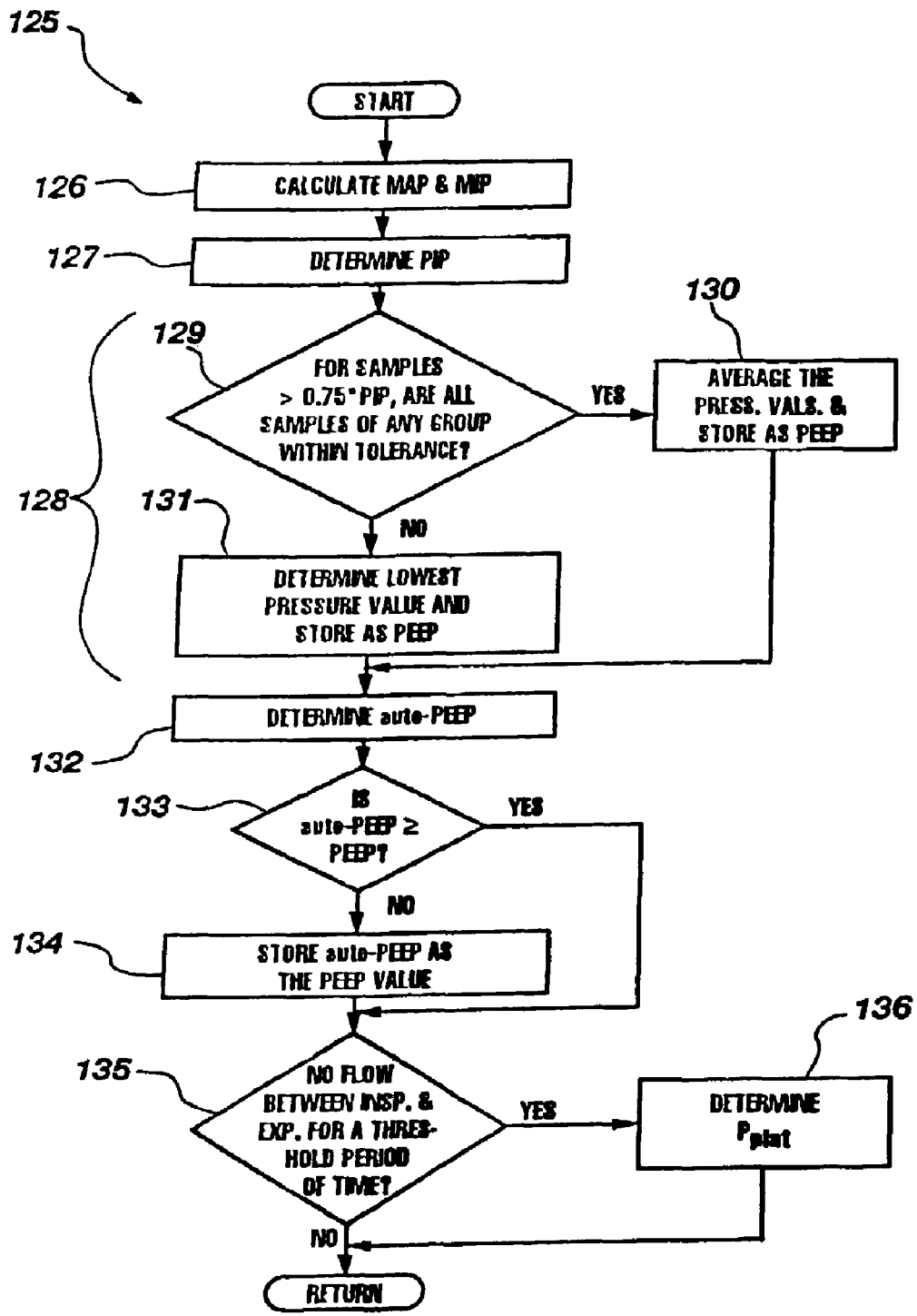
FIG. 6 is a flow chart of a method of calculating respiratory pressure parameters.

FIG. 6 is a flowchart which shows the steps involved in making various respiratory pressure calculations, collectively referred to as step 125. As shown at 126, the mean airway pressure (MAP) and mean inspiratory pressure (MIP) are calculated. MAP is calculated by averaging all of the stored, sampled pressure values over the last detected breath. MIP is calculated by averaging all of the stored, sampled inspiratory pressure values over the last detected breath. The largest absolute pressure value measured during the last detected breath, referred to as the peak inspiratory pressure (PIP), is determined as shown at 127. The positive end-expiratory pressure (PEEP) is determined as shown at 128.

The PEEP determination, which is made as shown at 128, begins from the point where the respiratory pressure falls to about 75% of the latest PIP value. While the respiratory pressure remains below about 75% of the latest PIP value, a determination is made about whether all of the sampled pressures within each 50 millisecond (0.05 sec.) time period fall within a predetermined tolerance, as shown at inquiry 129. If so, the values over that 50 millisecond time period are averaged, stored and designated as the PEEP value as shown at 130. If, due to high frequency breathing or unstable breathing, no 50 millisecond window of measured pressure values contains values which are within the set tolerance, the lowest measured pressure value is determined, stored and designated as the PEEP value as shown at 131.

Next, as shown at 132, the respiratory pressure value measured at air flow reversal (i.e., between exhalation and inhalation) is stored and designated as the auto-PEEP value. Preferably, the auto-PEEP value is equal to the pressure at a sample taken closest to the mid-point of air flow reversal. Auto-PEEP may also be determined by averaging the pressures of the last exhalation sample of a first breath and the first inhalation sample of the next breath. As shown at 133, it is determined whether the auto-PEEP value is greater than or equal to the PEEP value. If so, the PEEP value remains the same. If not, the auto-PEEP value is designated and stored as the PEEP value, as shown at 134. Auto-PEEP is considered to exist when inspiration occurs and the expired flow has not reached zero (i.e., no pause is apparent) because insufficient time has elapsed to allow the lung to passively deflate (as depicted in the respiratory flow waveform of FIG. 4).

If no respiratory flow is detected between inspiration and expiration for at least a threshold period of time, a plateau pressure value ($P_{plat}$) is then determined and stored. Long no-flow periods are common during mechanical ventilation of a patient. If, as shown at inquiry 135, it is determined that the no-flow duration met or exceeded a threshold amount of time, the respiratory pressure measurement of the sample at or nearest to the end of the no-flow period is designated and stored as the plateau pressure ($P_{plat}$), as shown at 136. If the no-flow duration was within the threshold time period, no $P_{plat}$ value determination is made or stored.

Figure 7:
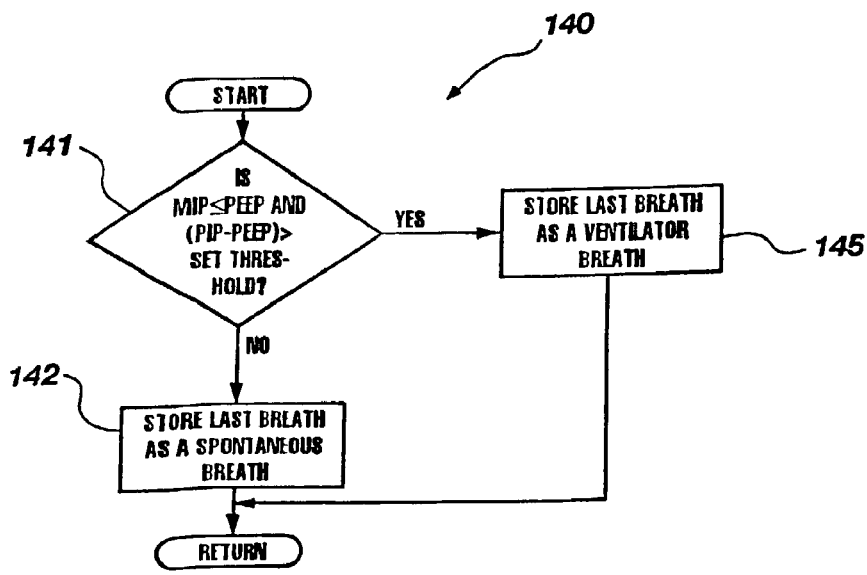
FIG. 7 is a flow chart of a preferred process for determining whether a patient breath was spontaneous or ventilator-induced.

FIG. 7 illustrates a preferred process 140 for determining whether the last detected breath was a spontaneous breath or a ventilator-induced breath. As shown at inquiry 141, the MIP and PEEP for the last detected breath are compared. Also at inquiry 141, process 140 determines whether the difference between PIP and PEEP is greater than a set ventilator pressure threshold. Preferably, the threshold pressure level is set to a default of 6 cm $H_2O$, and may be adjusted above or below that level. If the MIP is less than or equal to the PEEP and if the difference between PIP and PEEP is greater than the set threshold, the last detected breath is designated and stored as a ventilator breath as shown at 142. If MIP is greater than the PEEP, or if PIP minus PEEP is less than or equal to the set threshold, the last detected breath is designated and stored as a spontaneous breath as shown at 145.

Figure 8:
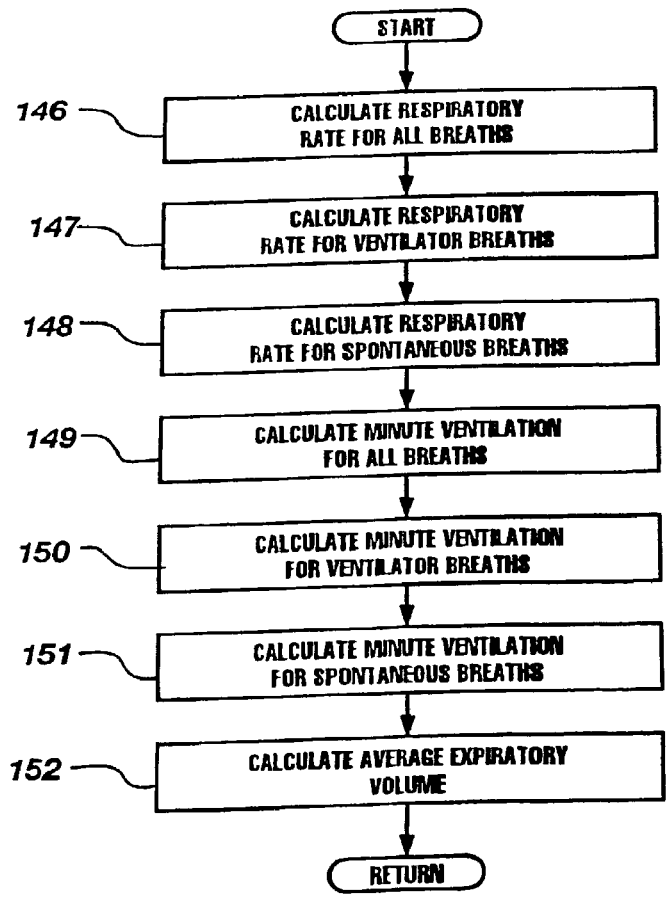
FIG. 8 is a flow chart of a method of calculating various respiratory rate and minute ventilation parameters.

Referring to FIG. 8, the respiratory rates, also referred to as respiratory frequency, for all breaths, for ventilator breaths, and for spontaneous breaths are measured as shown at 146, 147 and 148, respectively. The frequency of each breath is equal to $60/T_{tot}$, which supplies a value in units of breaths per minute. Preferably, each of the respiratory frequency values is determined by averaging the frequency values for the last eight breaths of each respective breath type (i.e., total, ventilator and spontaneous breaths).

Minute ventilation, the total quantity of gas exhaled by a patient over a time period of one minute, is calculated for the total volume exhaled, the volume exhaled during ventilator breathing, and the volume exhaled during spontaneous breathing as shown at 149, 150 and 151, respectively. Preferably, the minute ventilation calculations are equal to the average of $V_e$ divided by $T_e$ for each of the last eight detected breaths of a specific type. The minute ventilation calculations are preferably updated with each detected breath.

Figure 10:
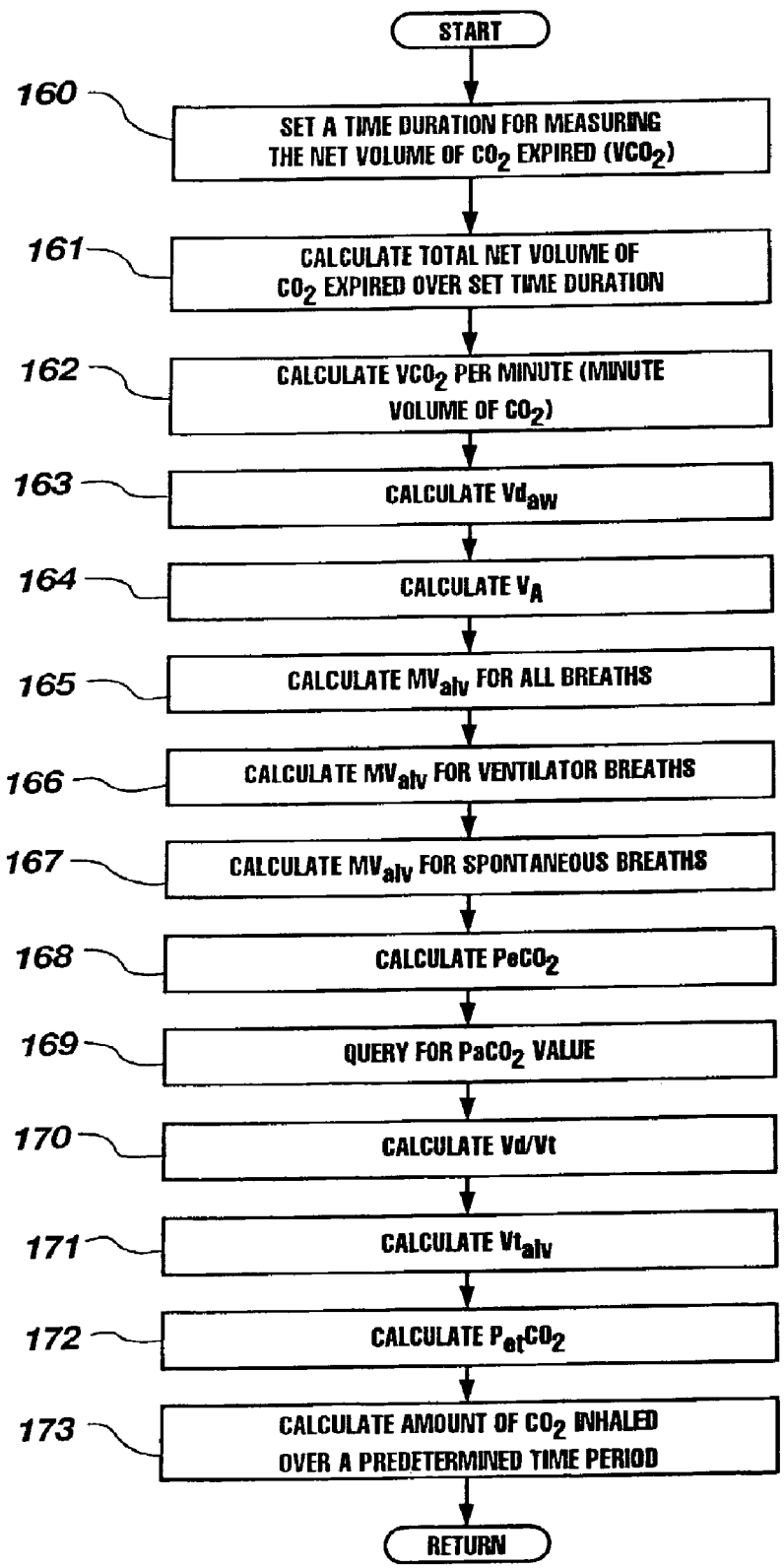
FIG. 10 is a flow chart of a method of calculating various respiratory carbon dioxide parameters.

Referring to FIG. 10, the preferred method according to the present invention calculates several values related to levels of $CO_2$ exhaled and the amount of deadspace. One such value, the volume of $CO_2$ exhaled per minute, is determined by calculating, as shown at 161, the net volume of $CO_2$ exhaled for each breath over a set time duration, which is set as shown at 160. As shown at 161, the percent $CO_2$ is multiplied by the total volume inhaled and exhaled (i.e., the tidal volume) over a detected breath. That value is reduced by the inspired volume of $CO_2$ (i.e., $CO_2$% inhaled multiplied by $V_i$), then multiplied by one unit time and divided by the set duration of the detected breath (in either units of time or breath) to determine the net volume of $CO_2$ that was expired by the patient over the set duration ($V_{CO_2e}$). A preferred equation for calculating the volume of $CO_2$ exhaled per minute follows:

$$V_{CO_2e} = \Sigma FCO_2 \times V \times \Delta t,$$

where $FCO_2$ is the fraction of $CO_2$, V is the flow rate, and $\Delta t$ is the change in time. As shown at 162, the $V_{CO_2}$ values for each detected breath are then averaged over the duration set in step 160 above to provide an exhaled $CO_2$ value per minute. If the selected duration is a time duration, the value for the amount of $CO_2$ exhaled per unit of time is preferably updated at discrete time intervals. Preferably, the volume of $CO_2$ exhaled per unit of time is updated at least about every fifteen seconds. If the selected duration is calculated in number of breaths, the value for the volume of exhaled $CO_2$ per breath is preferably updated with each detected breath. The volume of $CO_2$ expired per minute is commonly referred to as "$CO_2$ production" and "$CO_2$ elimination" since it represents the volume of $CO_2$ exhaled over the set duration.

Figure 9:
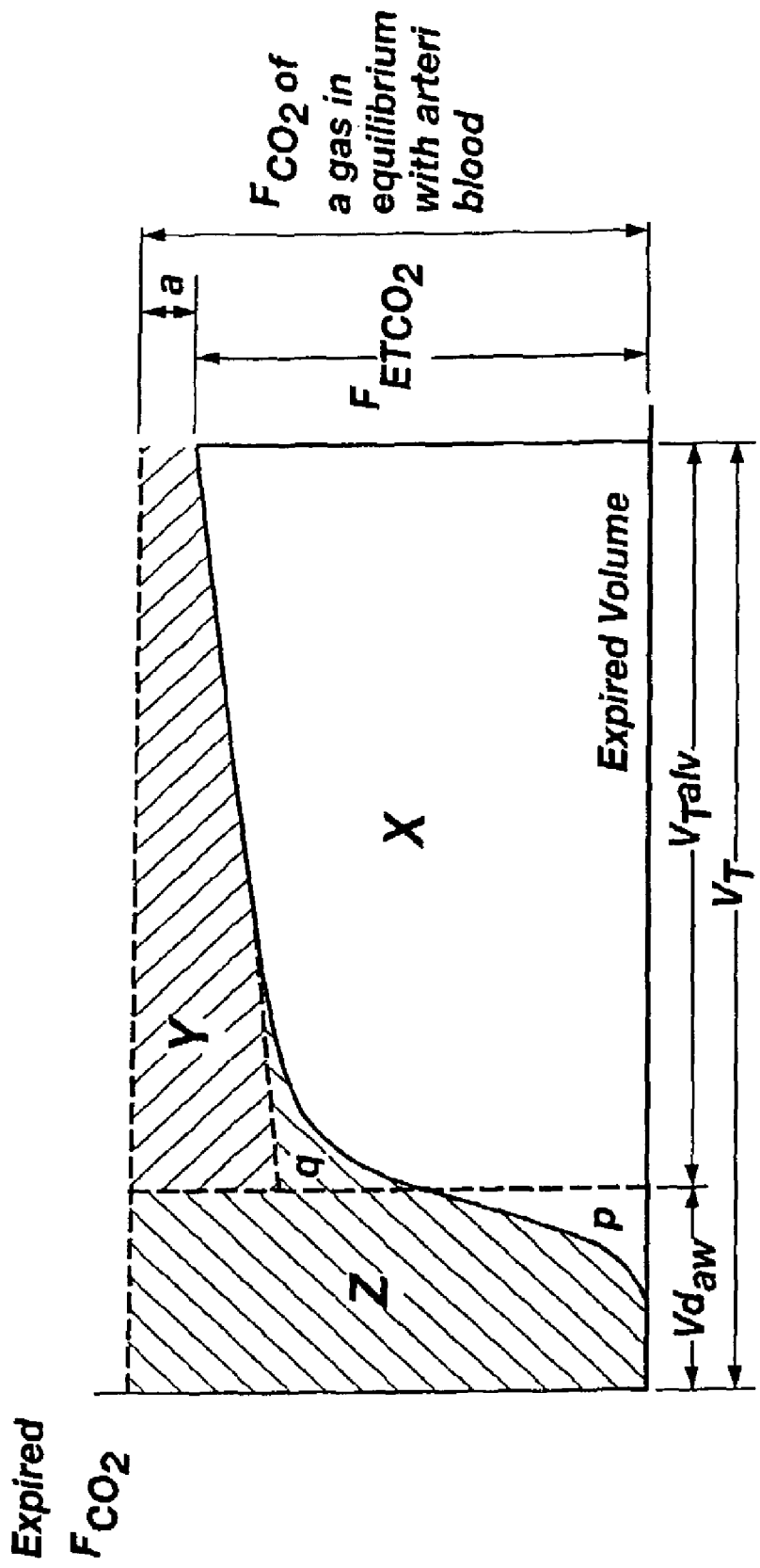
FIG. 9 is a graph which depicts the carbon dioxide fraction of expired gases plotted against a patient's total expired volume.

FIG. 9 is a graph which includes the carbon dioxide fraction of expired gas ($FCO_2$) on its y-axis and the total expired volume on its x-axis. The graph of FIG. 9 illustrates respiratory measurements, including carbon dioxide elimination, airway dead space and physiologic dead space. The character "a" represents the difference between the fraction of end tidal carbon dioxide ($ETCO_2$) and the arterial $FCO_2$. The Phase III slope is extrapolated to define the upper limit of "q". The area of "X" is equal to the volume of $CO_2$ in the expired breath. Areas "Y" and "Z" represent defects in carbon dioxide elimination, or wasted ventilation due to airway (anatomic) dead space ($Vd_{aw}$) and alveolar volume ($Vt_{alv}$). The location of the dividing line between $Vd_{aw}$ and $Vt_{alv}$ is determined by the areas of "p" and "q" which are equal. The areas of "p" and "q"

are equal to the airway dead space. Thus, $Vd_{aw}$ and $Vt_{alv}$ are dependent upon and may be determined from the $FCO_2$ and the slope of the Phase III line.

The airway dead space, also referred to as the anatomic dead space, Fowler's Dead Space, or the ineffective tidal volume, is calculated as shown at 163. Anatomic dead space is the volume of gas that fills the airways following the inspiratory phase. The tidal volume is equal to the anatomic dead space plus the amount of gas coming from the alveoli. Preferably, Aitken and Clark-Kennedy's method for measuring anatomic dead space is employed. In Aitken and Clark-Kennedy's method, the Phase III slope is extrapolated, as represented in FIG. 9 by the diagonal dashed line. A vertical dividing line, represented in FIG. 9 by the vertical dashed line, is then positioned along the inclining portion of the fraction of expired $CO_2$ plot such that it intersects the Phase II line at a point where the areas marked "p" and "q" are equal. The expired volume value upon which the dividing line is located (along the x-axis) is the volume of anatomic dead space. Preferably, a linear regression is computed of the points bounded by 30 to 70% of expired $CO_2$ volume to determine the appropriate location for the dividing line.

More specifically, a threshold level of $CO_2$ is detected by finding the point where the curve transcends from a value below 0.5% to a value above 0.5%. In the instant invention, this point is used as the initial point of Phase II. From the threshold point, subsequent $CO_2$ data points are adjoined and tested for linearity to the data point where the signal deviates from a linear path. The amount of allowed deviation is typically 5% in adults. The point where the deviation occurs marks the termination of Phase II and the slope of the Phase II segment is derived. As described further herein, the Phase II slope is used later. The slope of Phase III is determined in an analogous manner by starting at the last data point of expiration ($P_{et}CO_2$) and regressing toward the termination point of Phase II. Once the Phase II and III slopes are computed, the remaining input variables are derived as the following:

TABLE I

| | |
|---|---|
| $Vd_{aw}$ | The anatomic dead space volume is determined by examining the volume that gives equal area between the start of the Phase II data and the start of the Phase III data. This computation is done by fractional difference. (Fowler W. S. Lung Function Studies II. The Respiratory Dead Space. *Am. J. Physiol.* 154: 405, 1948 - the teachings of which are hereby incorporated by reference). |
| $P_{et}CO_2$ | The end tidal value of $pCO_2$. The last element in the $CO_2$(vol) data array is used for $P_{et}Co_2$. |
| $V_e$ | The total volume of air exhaled expressed in ml. |

Next, referring again to FIG. 10, as shown at 164, the alveolar tidal volume ($V_A$), which is also referred to as the effective tidal volume, is calculated. Alveolar tidal volume is calculated by subtracting the anatomic dead space ($Vd_{aw}$) from the total tidal volume ($V_t$).

As shown at 165, the alveolar (effective) minute ventilation ($MV_{alv}$), which is the total quantity of gas exhaled from a patient's alveoli over a time period of one minute, is calculated. The alveolar minute ventilation is determined for each of total alveolar volume exhaled, the alveolar volume exhaled during ventilator breathing, and the alveolar volume exhaled during spontaneous breathing as shown at 165, 166 and 167, respectively. Preferably, the alveolar minute ventilation calculations are equal to the average of $V_A$ divided by $T_e$ (in minutes) for each of the last eight detected breaths of a specific type. The alveolar minute ventilation calculations are preferably updated with each detected breath.

The mixed expired carbon dioxide value (which is referred to as $PeCO_2$ when $CO_2$ is measured in units of mmHg or Kpa, and as $FeCO_2$ when $CO_2$ is measured in terms of percent) is determined as shown at 168 by dividing the volume of $CO_2$ in the breath by the mean expiratory volume, which was determined as shown at 118 of FIG. 3. Mixed Expired $CO_2$, as defined herein, is the volume-weighted eight breath average amount of $CO_2$ and is updated with every breath.

As shown at 169, the system queries the user for the patient's partial pressure of arterial carbon dioxide ($PaCO_2$). The physiologic dead space (Vd/Vt) is then calculated as shown at 170 in accordance with the following equation:

$$Vd/Vt=(PaCO_2-PeCO_2)/PaCO_2,$$

where $PaCO_2$ and $PeCO_2$ are the arterial and mixed expired $CO_2$, respectively. Preferably, the $PaCO_2$ value is user entered. However, it may also be determined in accordance with the method disclosed in U.S. Pat. No. 5,632,281, the disclosure of which is hereby incorporated by reference. Alveolar dead space ($Vt_{alv}$) is then determined, as shown at 171, by subtracting the anatomic dead space ($Vd_{aw}$) from the physiologic dead space (Vd/Vt).

The end tidal partial pressure of $CO_2$ ($P_{et}CO_2$) is calculated as shown at 172. Preferably, each 80 millisecond group of $CO_2$ samples (exemplary) during expiration is averaged. The largest 80 millisecond average is set as the $P_{et}CO_2$ value. The end tidal partial pressure of $CO_2$ may be determined on a breath-to-breath basis, or over a set period of time. Other floating time periods are also within the scope of the method of the present invention.

The amount of carbon dioxide inhaled by the patient is determined as shown at 173. The $CO_2$ samples in each 80 millisecond group of $CO_2$ samples over a set time duration are averaged. The smallest 80 millisecond average is set as the inspired $CO_2$ value. Samples within other time periods may also be used to calculated the amount of $CO_2$ inhaled by the patient. In the preferred method, this value is reported only when the $CO_2$ level remains greater than 3 mmHg for an entire 20 seconds.

Figure 11:
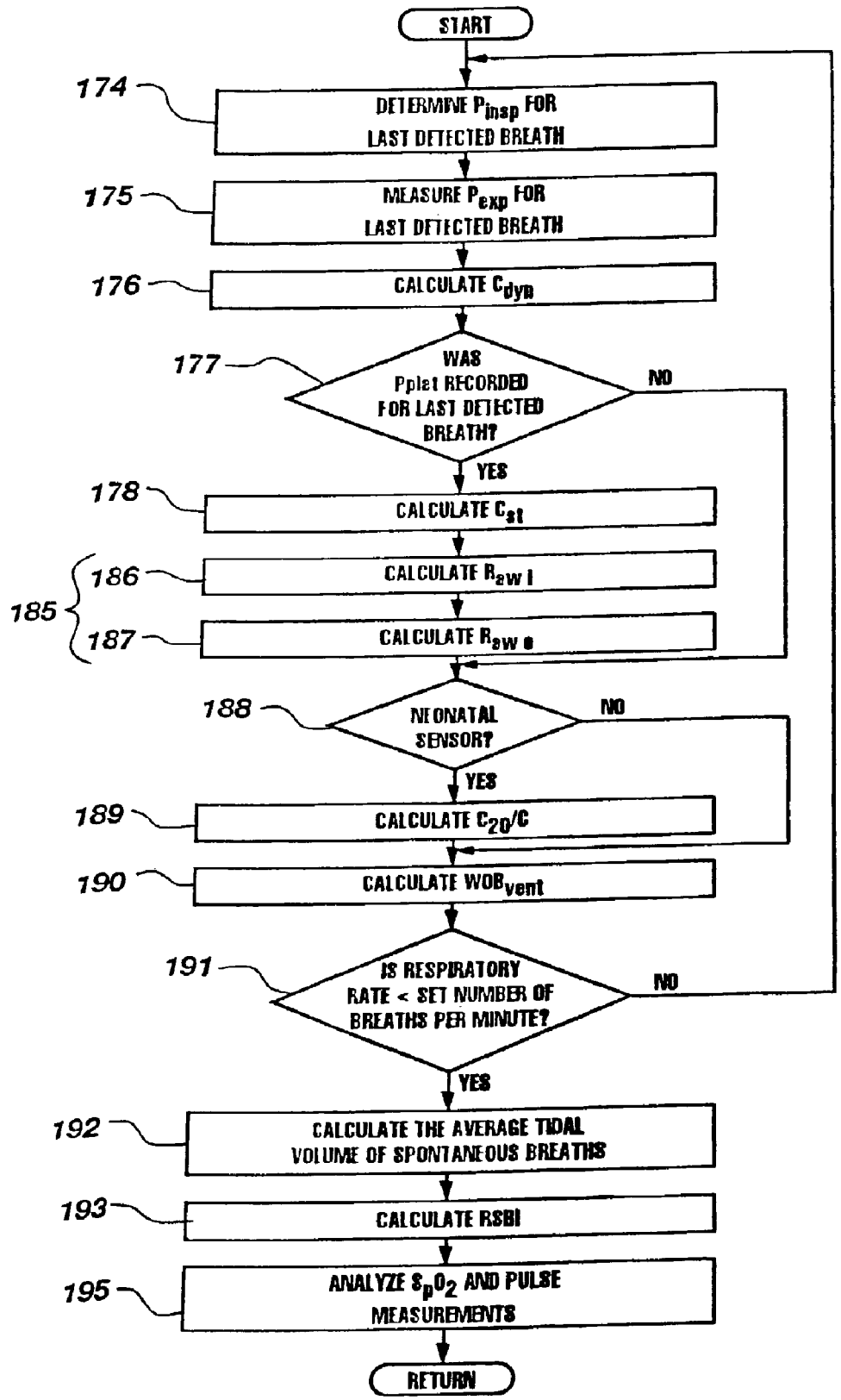
FIG. 11 is a flow chart of a method of calculating various respiratory mechanic parameters.

In instances where a respiratory ventilator controls a patient's breathing, certain respiratory mechanic parameters are measured and determined. FIG. 11 is a flow chart which illustrates a preferred process for determining respiratory mechanic parameters.

One such parameter, dynamic compliance ($C_{dyn}$), which is the ratio of the change in volume to the change in pressure during inspiration, is determined as shown at 176. At the point where flow crosses from inspiration to expiration (represented by circles in FIG. 4), the volume of inspired gases and the pressure, which is referred to as the initial inspiratory pressure ($P_{insp}$), are determined and stored as shown at 174. Flow also crosses or approaches zero after expiration. The volume at the point between inspiration and expiration is considered to be zero and the filtered pressure at that point, which is referred to as the initial expiratory pressure ($P_{exp}$) is measured and stored as shown at 175. The dynamic compliance is then computed, as shown at 176, as the ratio of the maximum inspiratory volume ($V_i$), determined as shown at 115 of FIG. 3, over the difference between $P_{exp}$ and $P_{insp}$. Preferably, $C_{dyn}$ is calculated by applying the least squares method to each respiratory sample over the entire breath.

As shown at 177, an inquiry is made about whether a $P_{plat}$ value was measured during the last detected breath. If not, the system proceeds to step 188. Otherwise, the system continues to step 178.

Static compliance ($C_{st}$) is calculated, as shown at 178, for mechanical breaths that have an inspiratory pause. $C_{st}$ is the ratio of the tidal volume at the beginning of the inspiratory hold (assumed to be at a maximum inspiratory tidal volume) divided by the difference between the plateau pressure ($P_{plat}$) and PEEP.

Airway resistance is determined as shown at 185. If a $P_{plat}$ value was measured during the last detected breath, as shown at 186, the airway resistance during inspiration ($R_{aw\ i}$) is calculated using the least squares method by subtracting the end inspiratory pressure (i.e., the pressure of the last inspiratory phase sample) from $P_{plat}$, then dividing that value by the air flow measured at the end of inspiration. Next, the airway resistance during expiration ($R_{aw\ e}$) is determined using the least squares method, as shown at 187. $R_{aw\ e}$ is the ratio of driving pressure during expiration to the maximum expiratory flow. First, the maximum expiratory flow sample value during the last detected breath is determined. Next, the maximum expiratory flow value is subtracted from the $P_{plat}$. That value is then divided by the maximum expiratory flow value for the last detected breath to provide a $R_{aw\ e}$ value. The system then proceeds to step 188.

As shown at 188, an inquiry is made of whether, as shown at inquiry 100 of FIG. 2, it was determined that samples are being taken with a neonatal respiratory sensor. If not, the system proceeds to step 190. If the respiratory samples are being taken with a neonatal sensor, the system of the present invention proceeds to step 189 to calculate compliance over the last 20% of the patient's breath/$C_{dyn}$ ($C_{20}$/C). First, the peak inspiratory pressure is multiplied by 80%; the product is the $P_{0.8max}$. The corresponding volume of gases inspired during the sampling with the closest pressure value is then determined and set as the $V_{P0.8max}$ value. $V_{P0.8max}$ is then subtracted from the inspiratory volume ($V_i$). That value is then divided by PIP less $P_{0.8max}$ to provide a $C_{20}$ value. $C_{20}$ is then divided by the $C_{dyn}$ value, obtained as shown at 176, to determine the $C_{20}$/C value.

As shown at 190, the ventilator's total inspiratory work of breathing ($WOB_{vent}$, which is measured in J/L) is determined. $WOB_{vent}$ is the work done by a ventilator on the respiratory system; it is the sum of the work required to ventilate the lung and the work required to move the chest wall of the relaxed or paralyzed patient. $WOB_{vent}$ is calculated by summing, during the entire inspiratory phase, the product of the driving pressure (airway pressure) at each respiratory sampling and the volume change from the last sample, where driving pressure is equal to the difference between the airway pressure of the sample less the PEEP value for the last detected breath (PEEP is considered baseline pressure). This work is then normalized to the inspiratory tidal volume. All of the work calculations involve the computation of areas using forms of work=integral over the specified time interval of P dv, where P is the driving pressure and dv is change in volume (or similarly PV dt, where PV is the product of the driving pressure and volume).

As shown at 191, an inquiry is made about whether the respiratory rate is less than a set number of breaths per minute. If not, the system of the present invention repeats the foregoing steps for the next breath or time interval. If so, the system proceeds to step 192. First, the average of the tidal volume of spontaneous breaths is determined by averaging the $V_e+V_i$ values for a set number (preferably eight) of the most recent spontaneous breaths, as shown at 192. As shown at 193, the rapid shallow breathing index (RSBI) is calculated. RSBI is equal to the respiratory rate (determined as shown at 146 of FIG. 8) divided by the average of the tidal volume of spontaneous breaths (determined as shown at 192).

As shown at 195, $SpO_2$ and pulse measurements are analyzed by the system of the present invention.

Data Display

The present invention also includes a display method, which comprises detecting a signal source and displaying data as indicated by the signal source. Signal sources include automatic sources such as warnings generated by the system and data which are always displayed, as well as user-input signals such as the parameter display keys that are disclosed in further detail below with reference to FIG. 13. The signals then direct the system to display data in the form of numeric values, graphical representations, or both.

Figure 12:
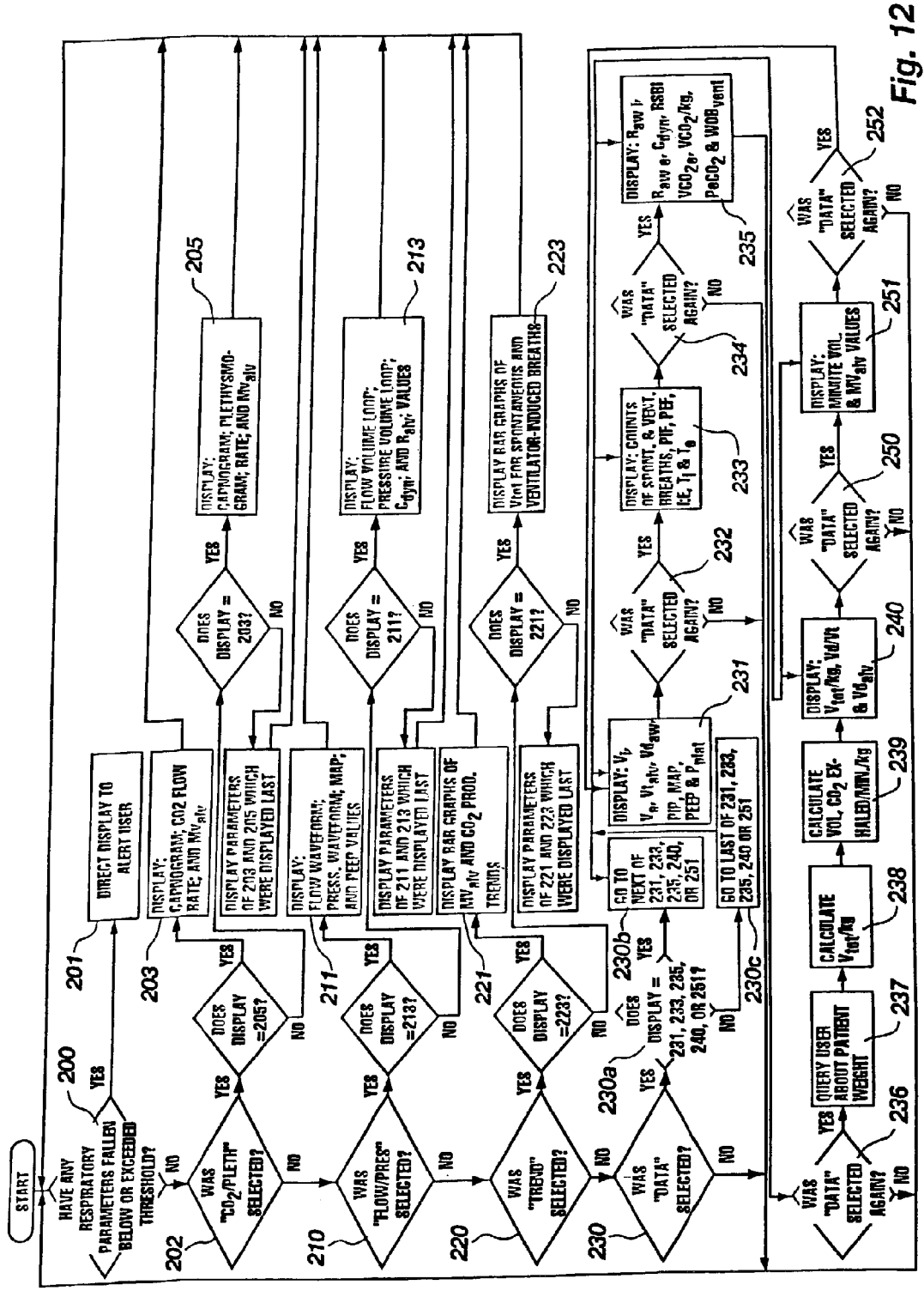
FIG. 12 is a flow chart of a preferred process of displaying respiratory profile parameters in accordance with another aspect of the present invention.

With reference to FIG. 12, in a preferred display method according to the present invention, as shown at 200, an inquiry is made about whether any of the measured or calculated respiratory parameters have fallen below the minimum threshold or exceeded the maximum threshold for that particular parameter. If so, the processing unit (reference character 18 of FIG. 1) sends the appropriate information and/or alerts to display, as shown at 201.

Preferably, alerts are generated for end tidal partial pressure of $CO_2$, respiration rate, $SpO_2$ and pulse rate. Minimum and maximum threshold values for each of these parameters are set by a user. As the end tidal partial pressure of $CO_2$, respiration rate, $SpO_2$ and pulse rate are determined, they are compared to the set thresholds. Sampled values which fall below their respective minimum threshold or exceed their respective maximum threshold trigger an alert. Similarly, the monitoring of and alerts for other parameters are also within the scope of the present invention.

The system of the present invention also alerts a user when the system has not detected respiration from a patient for a set length of time. Preferably, an alert is generated when the system has not detected respiration for a predetermined (e.g., twenty seconds) or user-selectable time duration.

The system of the present invention also displays various respiratory parameters, including, without limitation, the end tidal carbon dioxide level (determined as shown at 172 of FIG. 10) and the respiratory rate (determined as shown at 146 of FIG. 8). These parameters are preferably displayed at all times during which the monitor is not in a setup, configuration, or similar mode. The system of the present invention may also display parameters such as blood oxygen saturation ($SpO_2$) and pulse rate.

A preferred respiratory profile monitor for use with the present invention, such as that sold under the trademark $CO_2SMO$® Plus! by Novametrix shown in FIG. 13, includes parameter display keys 1301, 1302, 1303 and 1304 which direct the system to display other respiratory profile parameters. On the $CO_2SMO$® Plus! respiratory profile monitor, such keys are labeled "$CO_2$/Pleth" 1301, "Flow/Pres" 1302, "Trend" 1303 and "Data" 1304.

Referring again to FIG. 12, repeated and continual inquiries are made about whether any of the parameter display keys have been depressed. As shown at 202 of the flowchart, the system inquires whether the key labeled "$CO_2$/Pleth" has been pressed. If so, the system inquires whether any of the $CO_2$/plethysmogram displays are being shown (examples are described below). If not, the system shows the $CO_2$/plethysmogram display that was last shown. If so, the system shows the next $CO_2$/plethysmogram display. A first $CO_2$/plethysmogram display shows a capnogram (see FIG. 14) along with the flow rate of carbon dioxide and the alveolar minute volume, as shown at 203. A second $CO_2$/plethysmogram display shows a capnogram, a plethysmogram (see FIG. 15), the flow rate of carbon dioxide and the alveolar minute volume, as shown at 205.

Figure 16:
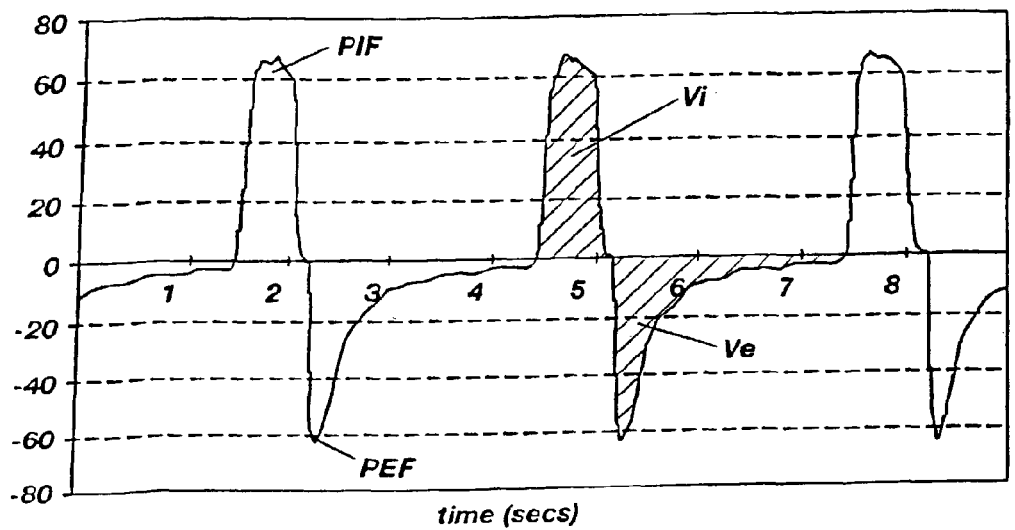
FIG. 16 depicts a flow waveform.
Figure 17:
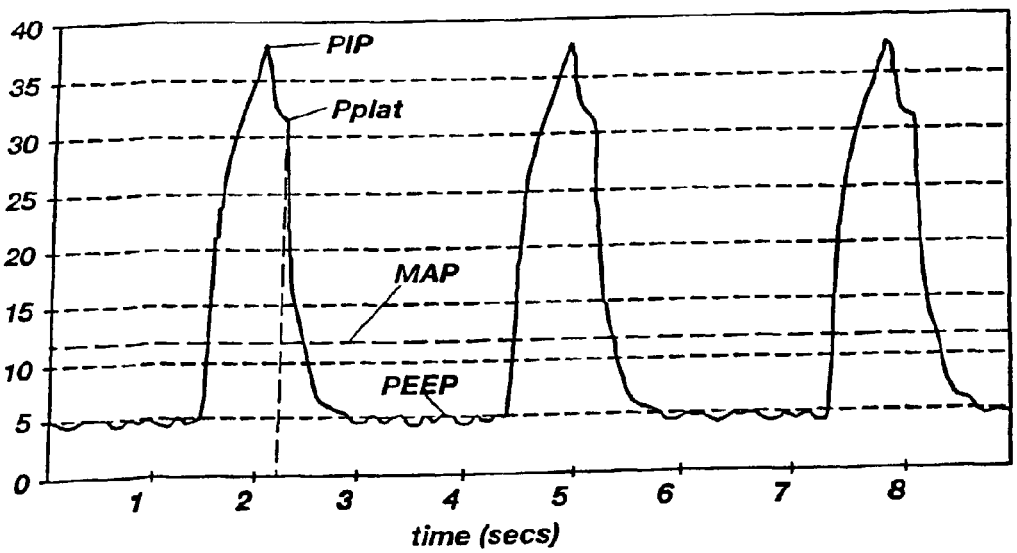
FIG. 17 depicts a pressure waveform.
Figure 18:
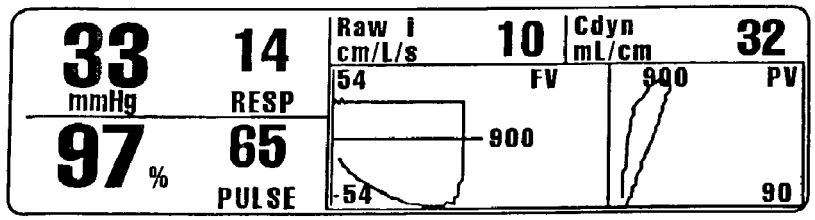
FIG. 18 depicts a flow-volume loop.
Figure 19:
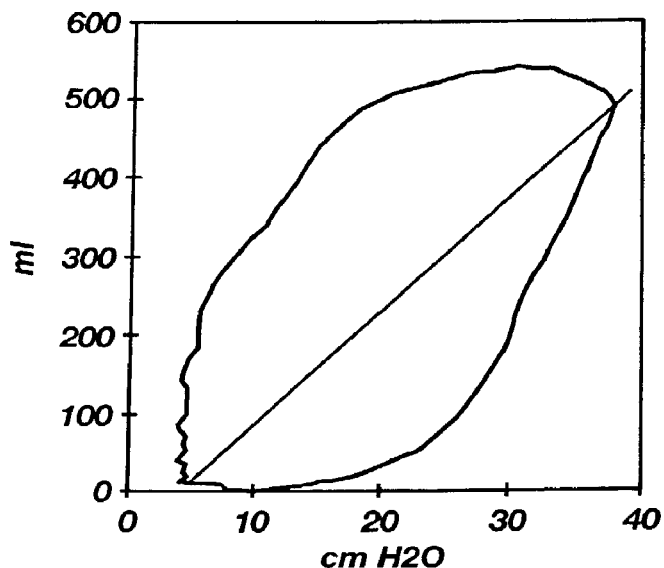
FIG. 19 depicts a pressure-volume loop.

Upon a depression of the "Flow/Pres" key, detected as shown at inquiry 210, the system inquires whether any of the flow/pressure displays are being shown (examples are described below). If not, the system shows the flow/pressure display that was last shown. If so, the system shows the next flow/pressure display. A first flow/pressure display shows a flow waveform (See FIG. 16) and a pressure waveform (See FIG. 17), and displays the MAP and PEEP values as shown at 211. A second flow/pressure display shows a flow volume loop (See FIG. 18), a pressure volume loop (See FIG. 19), $C_{dyn}$ and $R_{aw\,i}$ (if determined as shown at 176 and 186 of FIG. 11), as shown at 213.

When the "Trend" key is depressed, detected at inquiry 220, the system of the present invention inquires whether any of the trend displays are being shown (examples are described below). If not, the system shows the trend display that was last shown. If so, the system shows the next trend display. A first trend display shows, as depicted at 221, a bar graph illustrating the trend of alveolar minute ventilation and the trend of $CO_2$ production, each over a set time duration. Preferably, the alveolar minute ventilation trend graph illustrates both the spontaneous and mechanical ventilator components thereof. An exemplary time duration for illustration of such trends is twenty minutes. A second trend display shows bar graphs which illustrate the trends, or recent histories, of tidal volume attributable to ventilator-induced breathing and tidal volume generated by a patient's spontaneous breathing, as shown at 223.

Figure 20:
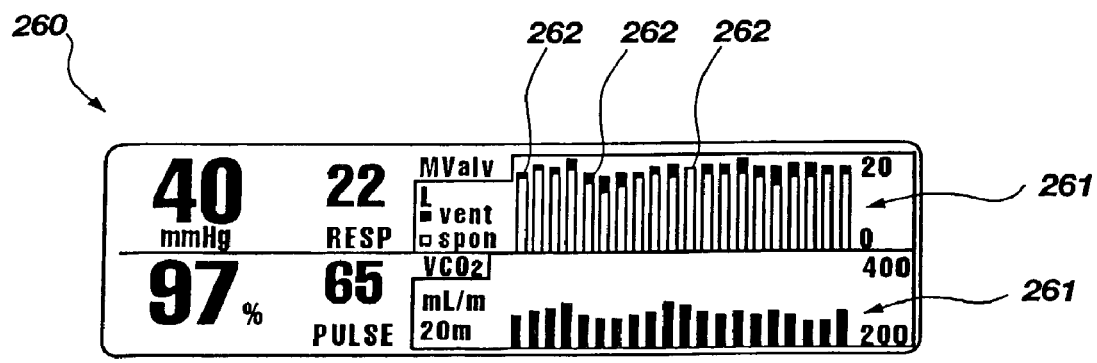
FIG. 20 illustrates a trend display according to the present invention.

All of the respiratory parameters may be stored for a set duration of time by processing unit 18 (See FIG. 1), which generates and displays trend bar graphs. With reference to FIG. 20, the trend display 260 illustrates the trend of a particular respiratory profile parameter over a set duration of time (e.g., 20 minutes, 1, 4, 8, 12 or 24 hours) as a set number of values (e.g., 10, 20). Each displayed value (i.e., a bar 262 of the bar graph 261) is representative of all of the corresponding measured respiratory profile parameter values over a particular time interval (e.g., an average value, median value, low value, high value, etc.). Preferably, all of the displayed values (i.e., bars 262) represent the corresponding measured respiratory profile parameter values over consecutive time intervals of equal length. For example, if the bar graph 261 includes twenty bars 262 which represent a respiratory profile parameter trend over the past 24 hours, each displayed value (i.e., a bar 262 of bar graph 261) represents all of the corresponding actual respiratory profile parameter values of each consecutive 1.2 hour interval.

When the key marked "Data" is pressed, detected as shown at inquiry 230, the system inquires whether any of the data displays are being shown (examples are described below). If not, the system shows the data display that was last shown. If so, the system shows the next data display. A first data display shows the following parameter values, as shown at 231: $V_i$, $V_e$, $Vt_{alv}$, $Vd_{aw}$, PIP, MAP, PEEP and $P_{plat}$. A second data display shows values for the number of spontaneous and ventilator-induced breaths, PIF, PEF, I:E ratio, $T_i$ and $T_e$ as shown at 233. A third data display shows, as depicted at 235, the $R_{aw\,i}$, $R_{aw\,e}$, $C_{dyn}$, RSBI, $VCO_2$, $VCO_2$/kg, $PeCO_2$ and $WOB_{vent}$ values. A fourth data display directs a user to enter the patient's weight at 237. Following entry of the patient's weight, the system calculates the corrected tidal volume as shown at 238. Corrected tidal volume is equal to the mean expiratory volume (determined as shown at 118 of FIG. 3) divided by the patient's weight. As shown at 239, the system of the present invention divides the exhaled $CO_2$ value by the patient's weight to determine the volume of $CO_2$ exhaled per minute per kilogram. The system of the invention then displays, as shown at 240, the following values: $V_{TOT}$/kg, Vd/Vt and $Vd_{alv}$. A fifth data display shows the spontaneous, ventilator-induced and total minute volumes and the spontaneous, ventilator-induced and total alveolar minute volumes as shown at 251.

Although the foregoing description contains many specificities, these should not be construed as limiting the scope of the present invention, but merely as providing illustrations of selected presently preferred embodiments. Similarly, other embodiments of the invention may be devised which do not depart from the spirit or scope of the present invention. The scope of this invention is, therefore, indicated and limited only by the appended claims and their legal equivalents, rather than by the foregoing description. All additions, deletions and modifications to the invention as disclosed herein which fall within the meaning and scope of the claims are embraced within their scope.

What is claimed is:

1. Apparatus for monitoring and displaying data obtained from respiration of an individual, comprising:
    at least one respiratory monitor; at least one processing element in communication with said at least one respiratory monitor and configured to:
    evaluate a signal generated by said at least one respiratory monitor while monitoring at least one respiration of the individual;
    calculate at least one respiratory parameter based on said signal; and
    estimate at least one blood gas parameter based on at least one of said signal and said at least one respiratory parameter.

2. The apparatus of claim 1, further comprising: at least one display element in communication with at least one of said at least one processing element and said at least one respiratory monitor.

3. The apparatus of claim 2, wherein said at least one display element comprises an indicator configured to display at least one respiratory parameter and said at least one blood gas parameter.

4. The apparatus of claim 3, wherein said indicator comprises a numeric component.

5. The apparatus of claim 3, wherein said indicator comprises a graphic component.

6. The apparatus of claim 5, wherein said graphic component is configured to display a bar graph.

7. The apparatus of claim 6, wherein at least one bar of said bar graph includes a first component and an adjacent, discrete second component.

8. The apparatus of claim 7, wherein said first component represents a first respiratory parameter and said second component represents a second respiratory parameter.

9. The apparatus of claim 8, wherein said first respiratory parameter comprises a portion of a breath by the individual that was effected by a mechanical ventilator and said second respiratory parameter comprises a portion of a breath effected by the individual.

10. The apparatus of claim 1, wherein said at least one respiratory monitor comprises a respiratory flow monitor.

11. The apparatus of claim 1, wherein said at least one respiratory monitor comprises a respiratory gas monitor.

12. The apparatus of claim 11, wherein said respiratory gas monitor comprises a respiratory carbon dioxide monitor.

13. The apparatus of claim 1, wherein said at least one respiratory monitor comprises a respiratory flow monitor and a respiratory gas monitor.

14. The apparatus of claim 13, wherein said respiratory gas monitor comprises a respiratory carbon dioxide monitor.

15. Apparatus for monitoring and displaying data obtained from respiration of an individual, comprising:
  a respiratory flow monitor;
  a respiratory gas monitor;
  at least one processing element in communication with said at least one respiratory flow monitor and said at least one respiratory gas monitor and configured to:
  evaluate signals generated by each of said at least one respiratory flow monitor and said at least one respiratory gas monitor while monitoring at least respiration of the individual;
  calculate at least one respiratory parameter based on said signals; and
  estimate at least one blood gas parameter based on at least one of said signals and said at least one respiratory parameter; and at least one display element in communication with at least one of said at least one processing element, said at least one respiratory flow monitor, and said at least one respiratory gas monitor, said at least one display element being configured to show at least one displayed respiratory parameter and said at least one blood gas parameter.

16. The apparatus of claim 15, wherein said at least one display element is configured to show a number representative of at least one of said at least one displayed respiratory parameter and said at least one blood gas parameter.

17. The apparatus of claim 15, wherein said at least one display element is configured to show a graphic representation of at least one of said at least one displayed respiratory parameter and said at least one blood gas parameter.

18. The apparatus of claim 17, wherein said graphic representation comprises a bar graph.

19. The apparatus of claim 17, wherein at least one bar of said bar graph includes a first component and an adjacent, discrete second component.

20. The apparatus of claim 19, wherein said first component represents a first respiratory parameter and said second component represents a second respiratory parameter.

21. The apparatus of claim 20, wherein said first respiratory parameter comprises a portion of a breath by the individual that was effected by a mechanical ventilator and said second respiratory parameter comprises a portion of a breath effected by the individual.

22. The apparatus of claim 15, wherein said at least one respiratory gas monitor comprises a respiratory carbon dioxide monitor.

* * * * *